(12) United States Patent
DeLuca

(10) Patent No.: US 6,489,361 B1
(45) Date of Patent: *Dec. 3, 2002

(54) PHOSPHORUS BINDER

(75) Inventor: Hector F. DeLuca, Deerfield, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/649,710

(22) Filed: Aug. 25, 2000

Related U.S. Application Data

(63) Continuation of application No. 09/469,513, filed on Dec. 22, 1999, now Pat. No. 6,160,016.

(51) Int. Cl.⁷ .......................... A61K 31/19; A61K 33/42
(52) U.S. Cl. ........................................ 514/557; 424/602
(58) Field of Search ..................... 514/557; 424/602

(56) References Cited

U.S. PATENT DOCUMENTS

| | | | |
|---|---|---|---|
| 2,266,992 A | 12/1941 | Roblin, Jr. ................. 167/68 |
| 3,558,786 A | 1/1971 | Eriksson, et al. ........... 424/317 |
| 4,220,661 A | 9/1980 | Huitson ................. 424/317 |
| 4,851,221 A | 7/1989 | Pak et al. ................. 424/693 |
| 4,870,105 A | 9/1989 | Fordtran ................. 514/557 |
| 4,970,079 A | 11/1990 | Hem et al. ................. 424/646 |
| 5,393,535 A | 2/1995 | Kjems ................. 424/678 |
| 5,629,025 A | 5/1997 | Shockley et al. ........... 424/680 |
| 5,631,289 A * | 5/1997 | Abele ................. 514/557 |
| 5,637,312 A | 6/1997 | Tock et al. ................. 424/438 |
| 5,686,111 A | 11/1997 | Jalbert ................. 424/489 |

FOREIGN PATENT DOCUMENTS

| | | |
|---|---|---|
| EP | 0 260 390 A1 | 3/1988 |
| FR | 2.196.151 | 3/1974 |
| GB | 2196523 A * | 5/1988 |
| JP | 59154053 | 2/1986 |
| WO | WO 97/30601 | 8/1997 |

OTHER PUBLICATIONS

A. Ghazali, et al., "Management of Hyperphosphatemia in Patients with Renal Failure," Curr. Sci. pp. 566–579, 1993.

C. Xu, et al., "Effects of High Calcium Intake on Fat Digestion and Bile Acid Excretion in feces of Veal Calves," J. Dairy Sci. 81:2173–2177, 1998.

E. A. Slatopolsky, et al., "RenaGel®, a nonabsorbed calcium– and aluminum–free phosphate binder, lowers serum phosphorus and parathyroid hormone," *Kidney Internat.* 55:299–307, 1999.

* cited by examiner

*Primary Examiner*—Theodore J. Criares
*Assistant Examiner*—Jennifer Kim
(74) *Attorney, Agent, or Firm*—Quarles & Brady LLP

(57) ABSTRACT

A calcium formate composition for oral administration to an individual for the purpose of inhibiting gastrointestinal absorption of phosphorus is disclosed. A method of inhibiting gastrointestinal absorption of phosphorus, comprising administering orally the composition, preferably close in time to food and beverage consumption is also disclosed.

6 Claims, No Drawings

PHOSPHORUS BINDER

CROSS-REFERENCE TO RELATED APPLICATION

This application is a continuation of U.S. application Ser. No. 09/469,513, filed Dec. 22, 1999, now U.S. Pat. No. 6,160,016.

STATEMENT REGARDING FEDERALLY SPONSORED RESEARCH OR DEVELOPMENT

BACKGROUND OF THE INVENTION

Phosphorus retention plays a major role in chronic renal failure in the development of both secondary hyperparathyroidism and osteodystrophy. Bricker, N., S. et al., *Archives of Internal Medicine* 123:543–553 (1969); Rubini, M. E. et al., *Archives of Internal Medicine* 124:663–669 (1969); Slatopolsky, E., et al., *Journal of Clinical Investigation* 50:492–499 (1971); Bricker, N. S., *New England Journal of Medicine* 286:1093–1099 (1972); Slatopolsky, E. S., et al., *Kidney Int.* 2:147–151 (1972).

Antacids are often used to bind dietary phosphorus to prevent phosphorus retention and prevent its absorption. This process is referred to as phosphorus binding and appears to be a chemical reaction between dietary phosphorus and the cation present in the binder compound, which is usually albumin or calcium. The binding results in the formation of insoluble and unabsorbable phosphate compounds, adsorption of phosphorus ions on the surface of binder particles, or a combination of both.

Presently-used antacids are inefficient at binding phosphorus in vivo. For example, a recent study by Ramirez, et al., noted that even though aluminum-containing or calcium-containing antacids were administered in large excess, they bound only 19–35 percent of dietary phosphorus. Ramirez, J. A., et al., *Kidney Int.* 30:753–759 (1986). Similar conclusions can be derived from data presented in earlier studies. Kirsner, J. B., *Journal of Clinical Investigation*, 22:47–52 (1943); Clarkson, E. M., et al., *Clinical Science* 43:519–531 (1972); Cam, J. M., et al., *Clinical Science and Molecular Medicine* 51:407–414 (1976); Man, N. K. et al., *Proceedings of the European Dialysis and Transplantation Association* 12:245–55 (1975).

Antacids are used widely, often in large quantities, for indigestion, heartburn or peptic ulcer disease. Despite their consumption in large amounts and often over long periods of time, phosphorus depletion is uncommon in these settings. This fact is additional evidence of the inefficiency of antacids as phosphorus binding agents.

The inefficiency of commonly used phosphorus binders creates a clinical dilemma. The dose of the binder must be increased to control hyperphosphatemia, but increased risk of toxicity of the binder results from the increased dose. This toxicity includes bone disease and aluminum dementia from aluminum-containing antacids and hypercalcemia and soft tissue calcification from calcium-containing antacids. These risks are particularly problematic in patients with chronic renal disease.

It would be very useful to have a phosphorus binder available which does not have the risks associated with ingestion of presently available binders. The binder should be more efficient in binding phosphorus and, thus, would not have to be consumed in the large quantities necessary, for example, when calcium carbonate-containing compositions are used. Such a phosphorus binder would be particularly valuable for administration to individuals with chronic renal failure, in whom phosphorus retention is a serious concern and the risk of toxicity from consumption of presently-available binders is greater than in individuals in whom kidney function is normal.

U.S. Pat. No. 4,870,105 addresses these concerns by disclosing a calcium acetate phosphorus binder. However, it would be advantageous to find a binder with a smaller anion and, hence, a smaller effective dose.

SUMMARY OF THE INVENTION

The present invention relates to a method of binding phosphorus in the gastrointestinal tract and, thus, reducing phosphorus absorption from the intestine. It also relates to a method of reducing serum phosphate levels because phosphorus bound in the gastrointestinal tract results in lower phosphorus absorption than would otherwise occur. It is particularly useful in the treatment and prevention of hyperphosphatemia in individuals with renal disease or other disease in which the ability to excrete phosphorus from the body (e.g., in the urine) is impaired.

The method of the present invention comprises orally administering to an individual a composition which includes calcium formate in sufficient quantity to effectively bind phosphorus, preferably present in food and beverages consumed by the individual, and prevent its absorption in the intestine. In an advantageous form of the invention, the calcium formate is administered at a dose of between 0.5 and 10.0 grams.

The present invention is also a pharmaceutical composition comprising calcium formate in combination with a pharmaceutically acceptable carrier. In a preferred embodiment, the composition comprises 0.5 grams of calcium formate per capsule or tablet. In another preferred embodiment, the composition comprises calcium formate and at least one additional therapeutic ingredient. In a most preferred embodiment, this therapeutic ingredient is a vitamin D compound, typically cholecalciferol.

It is a feature of the present invention that the amount of calcium-containing compound sufficient to inhibit gastrointestinal phosphorus absorption is 10% lighter than therapeutically equivalent amounts of previously known calcium acetate compounds.

Other objects, features and advantages of the present invention will become apparent to one of skill in the art after review of the specification and claims.

DETAILED DESCRIPTION OF THE INVENTION

The present invention relates to a calcium formate composition for oral administration to an individual. The composition is useful in reducing phosphorus absorption in the gastrointestinal tract. Calcium formate is shown below to be effective in inhibiting phosphorus absorption when administered orally in in vivo tests and has been shown to prevent the absorption of ingested phosphorus at a lower dose than other calcium-containing binders. As a result of these discoveries, calcium formate, alone or in combination with other materials, can be used to bind phosphorus in the gastrointestinal tract, thus reducing the percentage of an amount of phosphorus consumed (i.e., of a given "dose" of phosphorus) which is absorbed. Preferably, this dose would be 0.5–10.0 grams when adjusted to doses intended for human patients.

The present invention also relates to a method of inhibiting gastrointestinal phosphorus absorption. The method of the present invention is based on the demonstration that calcium formate is an effective binder of phosphorus when administered orally to an individual. The method comprises orally administering a quantity of calcium formate sufficient to bind with phosphorus in the gastrointestinal tract. Preferably, this dose is between 10–200 milliequivalents of calcium and is preferably present in either tablet or gelatin capsule form. In a most preferable form of the present invention, the oral dose is ingested at mealtimes.

As a result of the present invention it is possible to administer calcium formate to reduce absorption of dietary phosphorus, which has the net effect of reducing the risks of adverse effects (e.g., bone disease and secondary hyperparathyroidism) observed in individuals (e.g., chronic renal patients) in whom the ability to excrete phosphorus in the urine is impaired.

As used herein, the term "phosphorus" includes phosphorus and phosphate in its various forms (e.g. $HPO_4^-$, $PO_4^{-3}$, etc.).

According to the method of the present invention, calcium formate is administered, alone or in combination with other substances (e.g., in a hard gelatin capsule; along with materials necessary to form a tablet or caplet as a delivery vehicle for the calcium formate; or along with a second phosphorus binder or other pharmaceutically useful substance) in sufficient quantities to reduce phosphorus absorption in the gastrointestinal tract. The calcium formate is administered orally, preferably close in time to food and beverage consumption. By "at mealtimes" we mean within 30 minutes of a meal.

In one embodiment, 0.5–10.0 grams of anhydrous calcium formate (11–44 milliequivalents calcium) is taken prior to food consumption (e.g., meal time) and a second dose of 0.5–10.0 grams of anhydrous calcium formate is taken after food consumption. The dose or quantity to be taken at a given time varies on an individual-by-individual basis and can be adjusted as needed (e.g., by monitoring serum concentration of phosphorus and calcium).

The present invention is also a pharmaceutical composition comprising calcium formate in a pharmaceutically acceptable carrier, wherein the calcium formate is present in an amount between 0.5–1.0 grams. In another embodiment, the pharmaceutical composition comprises calcium formate in amount suitable to inhibit gastrointestinal absorption of phosphorus, provides between 11 and 44 milliequivalents of calcium, and is 10% lighter than the corresponding calcium acetate dose. By "corresponding" or "therapeutically equivalent," we mean a dose that is equally effective.

In another embodiment of the present invention, the pharmaceutical composition essentially comprises only calcium formate and at least one pharmaceutically carrier, wherein the calcium formate is present in an amount sufficient to produce between 11 and 44 milliequivalents of calcium. By "essentially comprises" we mean that calcium formate is the only active ingredient in the pharmaceutical composition.

The present invention is also a pharmaceutical composition comprising calcium formate in a pharmaceutically acceptable carrier combined with other therapeutic agents, preferably a vitamin D compound. Most preferably, the calcium formate is combined with vitamin D is cholecalciferol in a range of 125 IU to 400 IU in a tablet or capsule.

EXAMPLE I

Calcium Formate as a Phosphate Binder in Normal Rats

TABLE 1

| Group | % Ca Formate | Phosphorus (mg %) (mean ± SEM) | Weight | Serum Ca (mg %) (mean ± SEM) |
|---|---|---|---|---|
| | | 1 Week on Diet | | |
| 1 | 0 | 4.96 ± .48 | 209 ± 5.5 | ND |
| 2 | 1 | 3.25 ± .31 | 229 ± 5.5 | ND |
| 3 | 2 | 2.50 ± .32 | 211 ± 6.3 | ND |
| 4 | 3 | 2.5 ± .20 | 194 ± 6.5 | ND |
| | | 2 Weeks on Diet | | |
| 1 | 0 | 5.98 ± .39 | 295 ± 4.8 | 11.4 ± .20 |
| 2 | 1 | 4.70 ± .62 | 211 ± 3.8 | 14.0 ± .51 |
| 3 | 2 | 2.7 ± .24 | 198 ± 5.2 | 12.8 ± .94 |
| 4 | 3 | 2.9 ± 0.8 | 150 ± 8.0 | 12.9 ± 1.3 |

ND = not determined. There were at least 6 rats per group.

Five-week-old Sprague Dawley rats were given a synthetic diet containing 0.47% Ca and 0.2% phosphorus for two weeks prior to the addition of calcium formate to the diet. Body weights were measured and blood serum was collected after one or two weeks on calcium formate.

The results of this experiment are tabulated in Table 1. All rats supplied with calcium formate had less serum phosphorus than control rats. There seemed to be little difference in serum phosphorus between rats on 2% or 3% calcium formate, thus indicating that a saturation binding point had been reached.

I claim:

1. A method for inhibiting gastraintestinal absorption of phosphorous in an individusal, comprising:
   orally ingesting a quantity of calcium formate sufficient to bind with phosphorous in the gastrointestinal tract, wherein the calcium formate is present in an amount sufficient to provide between 10–200 milliequivalents of calcium and wherein the calcium formate is present in either tablet or capsule form.

2. The method of claim 1 wherein the calcium formate provides between 11 and 44 milliequivalents of calcium.

3. The method of claim 1 wherein the calcium formate is orally ingested in a first and second dose, wherein the first dose is before a mealtime and the second dose is after a mealtime.

4. A method for inhibiting gastrointestinal absorption of phosphorous in an individual, comprising:
   orally ingesting a quantity of calcium formate at mealtimes, wherein the calcium formate is present in an amount sufficient to provide between 10–200 milliequivalents of calcium and wherein the calcium formate is present in either tablet or capsule form.

5. The method of claim 4 wherein the amount of calcium formate provides between 11 and 44 milliequivalents of calcium.

6. A method of reducing blood serum phosphorus level, comprising the step of:
   orally ingesting a quantity of calcium formate at mealtime sufficient to inhibit gastrointestinal absorption of phosphorus in an individual, wherein the calcium formate is present in an amount sufficient to provide between 10–200 milliequivalents of calcium and wherein the calcium formate is present in either tablet or capsule form.

* * * * *

UNITED STATES PATENT AND TRADEMARK OFFICE
CERTIFICATE OF CORRECTION

PATENT NO.    : 6,489,361 B1
DATED         : August 25, 2000
INVENTOR(S)   : Hector F. DeLuca It is certified that error appears in the above-identified patent and that said Letters Patent is hereby corrected as shown below:

Column 4,
Line 33, "gastraintestinal" should read -- gastrointestinal --.

Signed and Sealed this

Eleventh Day of March, 2003

JAMES E. ROGAN
*Director of the United States Patent and Trademark Office*